(12) United States Patent
Lee et al.

(10) Patent No.: US 10,513,732 B2
(45) Date of Patent: Dec. 24, 2019

(54) SEQUENCING METHODS AND KITS

(71) Applicant: NEW YORK UNIVERSITY, New York City, NY (US)

(72) Inventors: Justin Lee, New York City, NY (US); Bhubaneswar Mishra, Great Neck, NY (US); Evgeny Nudler, New York City, NY (US)

(73) Assignee: New York University, New York, NY (US)

( * ) Notice: Subject to any disclaimer, the term of this patent is extended or adjusted under 35 U.S.C. 154(b) by 253 days.

(21) Appl. No.: 15/207,051

(22) Filed: Jul. 11, 2016

(65) Prior Publication Data

US 2017/0016062 A1    Jan. 19, 2017

Related U.S. Application Data

(60) Provisional application No. 62/191,627, filed on Jul. 13, 2015.

(51) Int. Cl.
*C12Q 1/6869*     (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

| | | | | |
|---|---|---|---|---|
| 6,010,850 A | * | 1/2000 | Weissman | C12Q 1/6809 435/6.18 |
| 2017/0016056 A1 | * | 1/2017 | Tan | C12Q 1/6855 |

OTHER PUBLICATIONS

Davey et al., "Genome-wide genetic marker discovery and genotyping using next-generation sequencing," Nature Reviews, Jul. vol. 12, pp. 499-510. (Year: 2011).*

Lou DI, et al., "High-throughput DNA sequencing errors are reduced by orders of magnitude using circle sequencing", Dec. 3, 2013, PNAS 110(49):19872-7.

Minoche AE, et al., "Evaluation of genomic high-throughput sequencing data generated on Illumina HiSeq and genome analyzer systems", Nov. 8, 2011, Genome Biology. 12:R112. doi: 10.1186/gb-2011-12-11-r112, PhiX-95nt experiment.

Garibyan L, et al., "Use of the rpoB gene to determine the specificity of base substitution mutations on the *Escherichia coli* chromosome" May 13, 2003, DNA Repair. 2(5):593-608.

Lang GI, et al., "Estimating the per-base-pair mutation rate in the yeast *Saccharomyces cerevisiae*", Jan. 2008, Genetics 178(1):67-82.

Newman, Aaron M. et al., "Integrated Digital Error Suppression for Improved Detection of Circulating Tumor DNA," Nat Biotechnol, vol. 34, No. 5, pp. 547-555, May 2016.

(Continued)

*Primary Examiner* — Young J Kim

(74) *Attorney, Agent, or Firm* — Hunton Andrews Kurth LLP

(57) ABSTRACT

A method for detecting rare genomic variants in a population of cells is disclosed. The method can detect de novo mutations in bacteria and analyze the impact of various physiological conditions on mutation rate, even though such effects would be too subtle to detect using other methods. The method can be used for detection of low-frequency subpopulations in the microbiome or in cancer.

9 Claims, 6 Drawing Sheets

Specification includes a Sequence Listing.

(56) References Cited

OTHER PUBLICATIONS

Gerstung, Moritz et al., "Reliable Detection of Subclonal Single-Nucleotide Variants in Tumour Cell Populations," Nature Communications, vol. 3, No. 811, pp. 1-8, 2012.
Lutz, Rolf et al., "Independent and Tight Regulation of Transcriptional units in *Escherichia coli* via the LacR/O and the TetR/O and AraC/I1-I2 Regulatory Elements," Nucleic Acids Research, vol. 25, No. 6, pp. 1203-1210, 1997.
Kinde, Isaac et al., "Detection and Quantification of Rare Mutations with Parallel Sequencing," PNAS, vol. 108, No. 23, pp. 9530-9535, Jun. 7, 2011.
Dwyer, Daniel J. et al., "Antibotics Induce Redox-Related Physiological Alterations as Part of Their Lethality," PNAS, pp. E2100-E2109, May 6, 2014.

\* cited by examiner

_US 10,513,732 B2_

SEQUENCING METHODS AND KITS

This application claims priority to U.S. Provisional Patent Application No. 62/191,627, filed Jul. 13, 2015. The entirety of the aforementioned application is incorporated herein by reference

FIELD

The present application relates generally to methods and kits for detection of genomic mutations.

BACKGROUND

The limiting factor to using high-throughput sequencing to directly analyze de novo mutations over a short time span is the error rate of sequencing machines and PCR. Whereas eukaryotes mutate less than 1 in $10^9$ bases per generation, the most accurate Illumina sequencing machines can misread 1 in 100 bases per generation. A number of recent methods have sought to lower this error rate. By introducing primers with random DNA "barcodes," it is possible to read redundant copies of an original genomic molecule and form a consensus sequence robust to sequencing machine errors. However, because of stochasticity in PCR amplification, this method can be of low yield, i.e. an average of 30× coverage is required for a single consensus sequence. The accuracy of this method is also limited by the accuracy of polymerases used for sample preparation PCR. These errors can be overcome using duplex barcoding. Further, even when a small region is targeted, duplexing results in lower yield than traditional barcoding, requiring on average 1000× coverage per consensus sequence. The mutational landscape of an entire RNA virus was recently mapped using "circle sequencing," but, the accuracy of this method is limited by the length of sequencing reads, which, for example, does not exceed 150 bp on an Illumina HiSeq.

Therefore, there exists a need for new techniques that may address the deficiencies in the existing methods for detection of genomic mutations.

SUMMARY

One aspect of the present disclosure relates to methods for sequencing and quantifying mutations in the genome of an organism. In one aspect, a method for sequencing mutations in the genome of an organism, comprising: (a) digesting genomic DNA of the organism with an enzyme that cleaves at the 3' end of the region of interest (ROI) to produce digested genomic DNA; (b) forming a linear amplification mixture comprising the digested genomic DNA and an adapter barcoded primer annealing at the 3' end of the ROI, and performing a single round of linear amplification to produce a single round linear amplification product; (c) performing N cycles of linear amplification with the single round linear amplification product and a forward adapter amplifier primer to produce a linear amplification product; (d) performing exponential polymerase chain reaction (PCR) with the linear amplification product to produce an amplified product; and (e) sequencing the amplified product. Further embodiments comprise the step of aligning the sequences obtained in step (e) to quantify mutations in the ROI. In other embodiments, the genomic DNA of the organism is digested with a restriction enzyme.

Another embodiment comprises the step of removing unused barcode primers from the single round linear amplification product. In a further embodiment, exponential PCR is performed by adding an adapter reverse primer and a reverse adapter primer to the linear amplification product. In certain embodiments, the adapter barcoded primer comprises an adapter region, a barcode region and an annealing region. In particular embodiments, the forward adapter amplifier primer shares a region of homology with an adapter region of the adapter barcoded primer.

In another aspect, a method for sequencing mutations in the genome of an organism, comprising the steps of: (a) cleaving a genomic DNA that contains one or more regions of interest (ROI), wherein the genomic DNA is cleaved at opposing locations relative to the one or more ROI; (b) ligating forked adapters to the opposite 3' ends of the genomic DNA, wherein the forked adapters comprise barcode DNA sequence; (c) forming a linear amplification mixture comprising the genomic DNA; (d) annealing adapter barcode primers to the 3' end of the forked adapters within the linear amplification mixture and performing one cycle of linear amplification with an adapter barcoded primer to yield a single round linear amplification product; (e) performing N cycles of linear amplification with a forward adapter amplifier primers; (f) performing exponential PCR with forward adapter amplifier primers, adapter-reverse-primer and reverse adapter amplifier primers to produce PCR products suitable for DNA sequencing. Further embodiments comprise the step of aligning the sequences obtained in step (e) to quantify mutations in the ROI. In other embodiments, the genomic DNA of the organism is digested with a restriction enzyme.

Another embodiment comprises the step of removing unused barcode primers from the single round linear amplification product. In a further embodiment, exponential PCR is performed by adding an adapter reverse primer and a reverse adapter primer to the linear amplification product. In certain embodiments, the adapter barcoded primer comprises an adapter region, a barcode region and an annealing region. In particular embodiments, the forward adapter amplifier primer shares a region of homology with an adapter region of the adapter barcoded primer.

In some aspects, the method can comprise one or more of the following procedures, e.g., (a) identifying one or a plurality of regions of interest (ROI) in the genome of the organism; (b) digesting genomic DNA of the organism with an enzyme that cleaves at the 3' end of the ROI to produce digested genomic DNA; (c) forming a first polymerase chain reaction (PCR) mixture comprising the digested genomic DNA and a barcoded primer annealing at the 3' end of the ROI, and performing a single round of linear amplification to produce a single round linear amplification product, wherein the barcoded primer comprises an adapter region, a barcode region and an annealing region; (d) removing unused barcoded primer from the single round linear amplification product; (e) performing N cycles of linear amplification with the single round PCR product and a forward adapter amplifier primer to produce a linear amplification product, wherein the forward adapter amplifier primer shares a region of homology with the adapter region of the barcoded primer; (f) adding an adapter reverse primer and a reverse adapter amplifier primer to the linear amplification product and performing exponential PCR to produce an amplified product; (g) sequencing the amplified product; and (h) aligning the sequences obtained in step (g) to quantify mutations in the ROI.

In other aspects, the method can comprise one or more of the following procedures, e.g., (a) digesting a genomic DNA with an enzyme that cleaves or nicks at the end of a region of interest (ROI); (b) forming a polymerase chain reaction (PCR) reaction mixture comprising the digested ROI; (c) annealing adapter barcode primers to the ROI within said reaction mixture and performing one cycle of linear amplification with the adapter barcode primer; (d) annealing forward adapter amplifier primers to said ROI within the reaction mixture and performing N cycles of linear amplification with the forward adapter amplifier primers; (e) annealing forward adapter amplifier primers, adapter-reverse-primer and reverse adapter amplifier primers to said ROI within the reaction mixture and performing exponential PCR to produce PCR products suitable for DNA sequencing; and (f) sequencing the PCR products and aligning the sequences obtained to quantify mutations in the ROI. In further aspects, the method can comprise comprising the steps of: cleaving at the 3' end of the ROI to produce digested genomic DNA with an enzyme that cleaves in two positions at opposite 3' ends of the ROI; ligating forked adapters to the opposite 3' ends of the ROI, wherein the forked adapters comprise double-stranded barcode DNA sequence; and performing linear amplification with adapter-amplifier primers that anneal only to the DNA sequence ligated to the 3' ending of the forked adapters.

In one aspect of the present disclosure, the enzyme can be a restriction enzyme. In another aspect, the enzymatic digestion can be performed with CRISPR/cas9. In another aspect, the digestion can be performed with a restriction endonuclease. In another aspect, the ROI is in the genome of a single-cell organism. In still another aspect, the single-cell organism is a bacterium. In yet another aspect, the bacterium can be *Mycobacterium tuberculosis* or *Escherichia coli*. In a further aspect, the barcode portion of the adapter barcode primer can have a sequence that is composed of 10-18 mer random barcodes in which either A, C, T, or G occurs at each location with equal probability. According to another aspect, the adapter barcode primer can have a barcode sequence that is composed of barcodes with AT/CG content optimized to minimize variation in amplification. According to another aspect, the barcode is a sequence up to 40 bp long with redundant random elements for robust indexing. In yet another aspect, N can be 8, 9, 10, 11, 12, 13, 14, 14, 16 or an integer greater than 16 and/or the ROI can be in the genome of a tumor cell. According to still further aspect, the tumor cell can be carcinoma, melanoma, lymphoma, blastoma, leukemia, myeloma, sarcoma or germ cell tumor. In yet another aspect, the tumor cell can be colorectal cancer or small-cell lung cancer. According to another aspect, the DNA that is sequenced and quantified for mutations is from circulating tumor cells or is cell-free DNA. According to another aspect, the DNA is from immune cells.

In another embodiment, a kit comprising adapter barcode primers, forward adapter amplifier primers, adapter-reverse-primer and reverse adapter amplifier primers for a ROI in the genome of an organism. In a further embodiment, a kit for performing comprising forked adapters, adapter barcode primers, forward adapter amplifier primers, adapter-reverse-primers and reverse adapter amplifier primers for a region of interest in the genome of an organism.

BRIEF DESCRIPTION OF THE DRAWINGS

The above and other objects and advantages of the application will be apparent upon consideration of the following detailed description, taken in conjunction with the accompanying figures and paragraphs.

Figure 1:
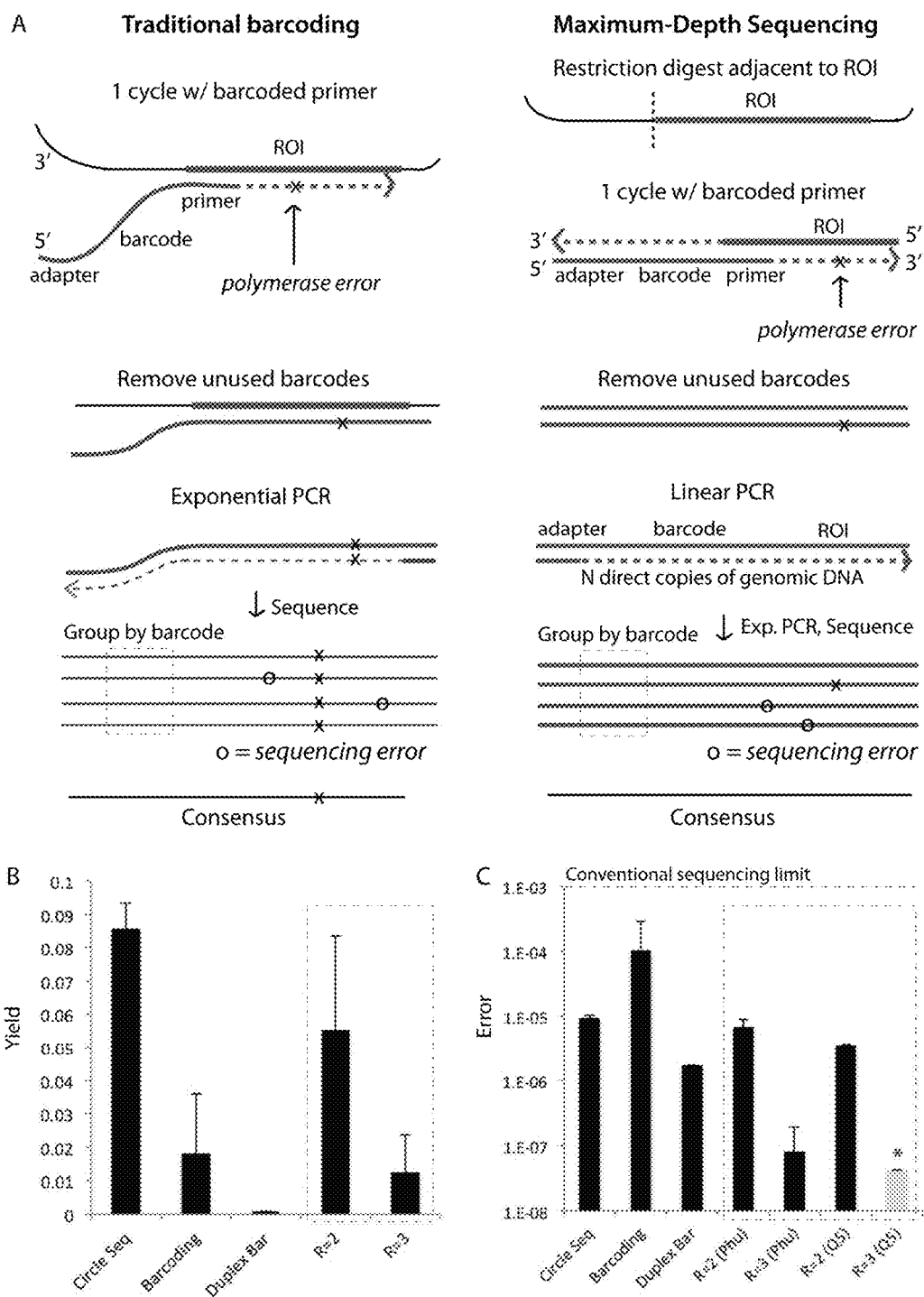
FIG. 1 is an exemplary MDS Overview. (Panel A) Comparison of traditional barcoding protocol with MDS. (Panel B) Mean yield of various methods, in consensus nucleotides called per nucleotides sequenced. Results from the study are boxed. (Panel C) Mean error rate of various methods when applied to in vitro synthesized DNA, in frequency of miscalled bases ($\log_{10}$ scale). Error rates from the study are given using both Phusion and Q5 polymerase. *Analysis of 1,685,502 consensus nucleotides yielded no errors. The value shown is extrapolated from the Q5 error rate and expected reduction given R=3. Yield and error rate from previous methods are from Lou, D. I. et al. High-throughput DNA sequencing errors are reduced by orders of magnitude using circle sequencing. PNAS 110(49):19872-7. Error bars are standard deviation.
Figure 2:
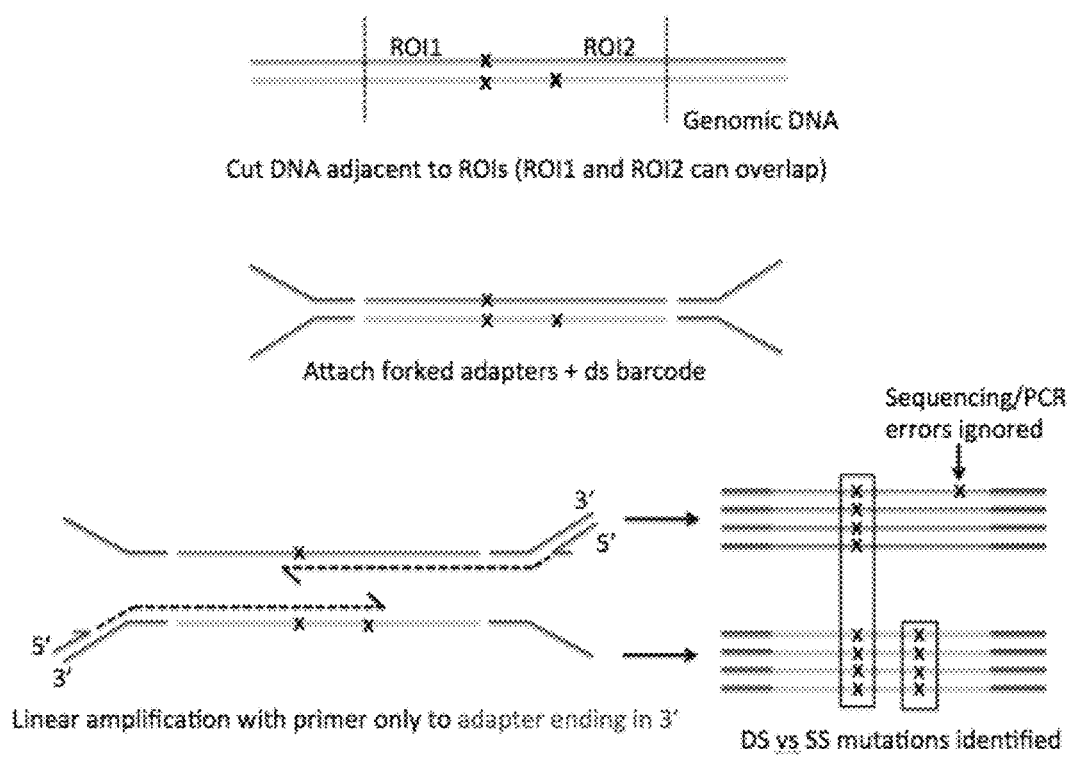
FIG. 2 is an illustration showing the combining of linear amplification of maximum depth sequencing with duplex barcode sequencing.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

Some modes for carrying out the present invention are presented in terms of its aspects, herein discussed below. However, the present invention is not limited to the described embodiment and a person skilled in the art will appreciate that many other embodiments of the present invention are possible without deviating from the basic concept of the present invention, and that any such work around will also fall under scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the enclosed paragraphs. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Maximum-Depth Sequencing

One aspect of the present disclosure relates to a method (hereinafter refers to as "Maximum-Depth Sequencing" or "MDS") for detecting extremely rare variants in any region of interest (ROI) in a population of cells. FIG. 1, panel A provides a schematic representation of the MDS process. First, genomic DNA is treated with a restriction enzyme, which cleaves at the 3' end of the ROI. A single PCR cycle is performed with barcoded primers annealing to the 3' end of the ROI. Because of the exposed 3' site on the genomic DNA molecule left by the restriction enzyme, the genomic DNA molecule acts as a "primer," causing the barcode and an adaptor to be synthesized onto the end of the ROI. This synthesis effectively attaches the barcode to the original genomic DNA molecule. Since the barcode/adapter are attached to the ROI through DNA polymerization, maximum depth sequencing is effective in combination with any restriction enzyme or random shearing technique, and is not limited to only the use of restriction enzymes with overhangs of a specific length as required by other approaches.

After the barcoded primer has been attached, unused barcoded primers are removed, and N cycles of linear amplification are performed using only primers to the forward adapter sequence. These forward adapter primers anneal to the adapter region of the barcoded primer, which has been specifically designed for that purpose. By not annealing the adapter primer to the ROI, this allows for more uniform amplification in multiplexed reaction and can reduce the degree of off-target amplification compared to other approaches. This linear amplification step is key to screening polymerase errors. The polymerase may make an error in any single round of synthesis, increasing the probability of generating a faulty read by N, but by copying the same original DNA molecule multiple times, the probability of recovering a defective copy after analysis is reduced by a factor of $N^R$, where R is the number of independent reads used to build a consensus sequence. Thus the total error reduction is $1/N^{(R-1)}$ fold (see FIG. 6 for details). In this study, typically N=12 and R≥3. Detailed error rate spectra for both Phusion and Q5 polymerase are measured and reported in Table 1 (Intrinsic sequencing and polymerase error probabilities, as well as empirical error rates for R=2. Sequencing error values from Minoche, A. E.; Dohm, J. C.; Himmelbauer, H. (2011) Evaluation of genomic high-throughput sequencing data generated on Illumina HiSeq and Genome Analyzer systems. Genome Biology. 12:R112. doi: 10.1186/gb-2011-12-11-r112, PhiX-95nt experiment).

TABLE 1

| Sub XY | CG | GC | AT | TA | AC | TG |
|---|---|---|---|---|---|---|
| Sequencing Error (Q > 20) | 0.002 | 0.0012 | 0.0012 | 0.0024 | 0.0036 | 0.0092 |
| Intrinsic Phusion Error | 7.7E−08 | 8.8E−07 | 2.5E−08 | 3.2E−08 | 2.8E−08 | 2.9E−08 |
| Intrinsic Q5 Error | 2.0E−08 | 3.1E−07 | 1.8E−08 | 2.0E−08 | 1.2E−08 | 2.1E−08 |
| Phusion Negative Ctrl R = 2 | 9.1E−09 | 8.5E−08 | 2.3E−08 | 1.5E−08 | 6.6E−09 | 4.4E−09 |
| Q5 Negative Ctrl R = 2 | 1.9E−09 | 2.0E−08 | 5.8E−09 | 2.8E−09 | 0.0E+00 | 1.6E−09 |

| Sub XY | CA | GT | AG | TC | CT | GA |
|---|---|---|---|---|---|---|
| Sequencing Error (Q > 20) | 0.0056 | 0.0028 | 0.004 | 0.0032 | 0.0024 | 0.0024 |
| Intrinsic Phusion Error | 2.1E−06 | 9.5E−08 | 3.9E−07 | 2.3E−07 | 1.6E−06 | 8.4E−07 |
| Intrinsic Q5 Error | 8.0E−07 | 4.3E−08 | 1.6E−07 | 4.5E−08 | 6.4E−07 | 2.4E−07 |
| Phusion Negative Ctrl R = 2 | 1.2E−07 | 2.0E−08 | 6.5E−08 | 4.2E−08 | 1.7E−07 | 9.3E−08 |
| Q5 Negative Ctrl R = 2 | 3.0E−08 | 6.3E−09 | 1.5E−08 | 6.1E−09 | 3.9E−08 | 2.9E−08 |

Figure 5:
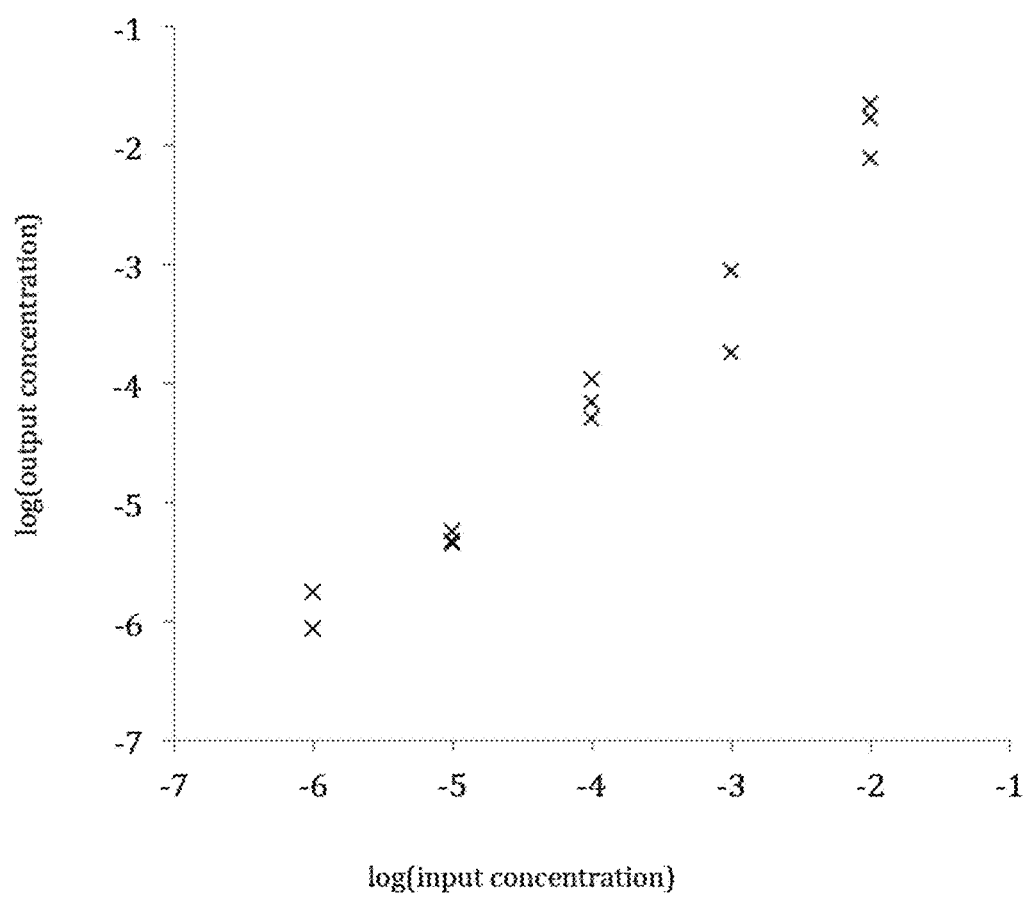
FIG. 5 is an illustration of a mock culture composed of rpoB point mutants of known concentration was sequenced using MDS. Output concentrations of each point mutant recovered from R=2 analysis are plotted against its input concentration (see Table 2 for details).

Because each read represents additional 1× coverage of the ROI, MDS can achieve ~$10^9$-fold coverage using an Illumina HiSeq machine. By targeting a ROI, it is also possible to use paired-end sequencing to increase yield. On mock cultures with single-nucleotide mutants spiked in at known concentrations, MDS reliably recovers the expected proportion of mutants even if their frequencies are as low as $10^{-6}$ (FIG. 5. MDS has yield equal to or greater than standard barcoding depending on the number of reads used to form a consensus sequence (FIG. 1, panel B) and reduces the error rate to less than $5 \times 10^{-8}$ per nucleotide sequenced, as shown on in vitro synthesized DNA templates (FIG. 1, panel C). It should be noted that when R>2, this error is derived almost entirely from transition substitutions typical of PCR polymerases, and that for other kinds of substitutions, error rate is virtually nonexistent. Even for transition substitutions, by increasing R, MDS can lower error rate indefinitely, given sufficient coverage. MDS does not require additional resequencing of barcodes as performed in other approaches, instead MDS uses short accurate reads of sequence to analyze not only the barcodes, but also the ROI itself. This increases the yield of the MDS protocol (in nucleotides per nucleotide sequenced) by a factor of over 100 compared to other approaches. MDS only requires two reads to call a consensus sequence with error rate <1%, while other approaches may require more than 300 reads.

In some aspects of the present disclosure, the method of the present disclosure can comprises the steps of (a) identifying a region of interest (ROI) in the genome of the organism; (b) digesting genomic DNA of the organism with an enzyme that cleaves at the 3' end of the ROI to produce digested genomic DNA; (c) forming a first polymerase chain reaction (PCR) mixture comprising the digested genomic DNA and a barcoded primer annealing at the 3' end of the ROI, and performing a single round of linear amplification to produce a single round linear amplification product, wherein the barcoded primer comprises an adapter region, a barcode region and an annealing region; (d) removing unused barcoded primer from the single round linear amplification product; (e) performing N cycles of linear amplification with the single round linear amplification product and a forward adapter amplifier primer to produce a linear amplification product, wherein the forward adapter amplifier primer shares a region of homology with the adapter region of the barcoded primer; (f) adding an adapter reverse primer and a reverse adapter amplifier primer to the linear amplification product and performing exponential PCR to produce an amplified product; and (g) sequencing the amplified product.

In other aspects, the method comprises the steps of: (a) digesting a genomic DNA with an enzyme that cleaves at the 3' end of a region of interest (ROI); (b) forming a polymerase chain reaction (PCR) mixture comprising the digested ROI; (c) annealing adapter barcode primers to the ROI within said reaction mixture and performing one cycle of linear amplification with the adapter barcode primer; (d) annealing forward adapter amplifier primers to said ROI within the reaction mixture and performing N cycles of linear amplification with the forward adapter amplifier primers; (e) annealing forward adapter amplifier primers, adapter-reverse-primer and reverse adapter amplifier primers to said ROI within the reaction mixture and performing exponential PCR to produce PCR products suitable for DNA sequencing; and (f) sequencing the PCR products and aligning the sequences obtained to quantify mutations in the ROI.

The enzyme can be any enzyme that is capable of cleaving or nicking a genomic DNA at the 3' end of a ROI. In some embodiments, the enzyme is an endonuclease. In some embodiments, the enzyme is a restriction enzyme. In other embodiments, the enzymatic digestion is performed by CRISPR/cas9.

The barcoded primer is an oligonucleotide comprising an adapter region, a barcode region and an annealing region. Optimal length of the adapter and amplifier sequences varies depending on the sequencing platform used. For an Illumina machine, an adapter region of 58 nt may be used. One of ordinary skill will understand that adapter regions may be as short as 20 nt or substantially longer depending on the sequencing platform. Neither the length or the composition of the adapter region is limiting on the invention. For the adapter amplifier primer, adapter-reverse primer, and reverse adapter amplifier primer, optimal length is similar to or shorter than those used for standard PCR (between 10 and 20 nt). The bar code region is a region of 6-40 nt. The annealing region is a region of 8-30 nt that is complementary to the 3' end of the ROI. Neither the length or the composition of the bar code region, nor the length or composition of the annealing region, is limiting on the invention. The adapter amplifier primer may have varying lengths and compositions as required by the protocol, including a barcode region within the adapter amplifier primer. More than one adapter amplifier primer may be used according to the targeted ROI and desired design of the MDS protocol. Other forms of barcodes (e.g. bisulfite, etc), or multiple barcodes, etc, are within the scope of this application. For example, a second barcoded primer may be used after the step of linear amplification.

In another aspect, after the sites around a given region of interest (ROI) (or pair of ROIs with spacer between them) have been cut (using restriction enzymes, CRISPR, or any number of random shearing techniques), ligation of forked adapters (with duplex barcode) to the ROI (or pair of ROIs) occurs. Forked adapters are assembled from pairs of nucleotide sequences in which the last section of the pair of nucleotide sequences (typically the last twelve nucleotides) are complementary to each other so that the pair can anneal in those positions. The forked adapters may then be ligated to the ends of genomic DNA molecules. At that point, linear amplification using a primer to only the prongs of the fork ending in 3' is performed. This enables maximum depth sequencing on both strands separately. After amplification (with or without additional exponential PCR) is complete, highly accurate consensus sequences from each strand are formed separately, or data is combined via the complementary barcodes to obtain a consensus sequence across both strands that is even more accurate than that obtained by duplex barcode sequencing alone (see FIG. 6. The linear amplification step performed in this embodiment is not possible in single-adapter approaches. This also allows for superior high-yield, straightforward selection of the target ROI as well as ease in alignment in downstream analysis not found in other methods. This embodiment also enables targeted, high-yield sequencing of any two ROIs that are on the same chromosome, which is not afforded by other approaches.

In certain aspects, maximum depth sequencing does not use restriction enzymes with overhangs of a specific length. In still further aspects, maximum depth sequencing does not use a primer that anneals to part of the region of interest. In other embodiments, maximum depth sequencing does not use sequencing of relatively long region of interest using a sequencing platform that has a higher error rate, but the capacity to produce long reads, such as Ion Torrent system. Maximum depth sequencing does not need to circumvent issues with misreading barcodes by performing an additional step of resequencing the barcodes only using a higher-fidelity sequencing machine that produces short reads, such as an Illumina machine. By contrast, maximum depth sequencing uses short accurate reads to analyze both the barcodes but also the region of interest itself.

In another aspect, a pair of restriction enzymes or CRISPR molecules are used to specifically cut DNA at two specific sites flanking the ROI (or pair of ROIs which may or may not overlap) on the same DNA molecule. In this approach, when duplex barcodes are ligated, they flank a region of a specific length with a specifically chosen sequence. The ROI can thus be selected using any number of size-selection techniques. In addition, alignment analysis post-sequencing is greatly simplified.

Applications of MDS

Bacterial Metagenomics

Gut microbiome composition has been associated with metabolic disorders including diabetes, autoimmune diseases, predisposition to esophageal and gastrointestinal cancers, variable drug metabolism, and infections associated with antibiotic-resistant gut microbes. Because of the sheer number of species in the gut, detection by culture or straight-forward qPCR is highly impractical. Comprehensive detection of species present in the gut through sequencing of 16S rRNA sequences, as would be enabled and improved by MDS, is expected to allow medical professionals to recommend diets and courses of antibiotic treatment, customized to prevent species associated with the aforementioned disorders from proliferating in an individual. Furthermore, it has been shown that ~100 bp regions of DNA, such as those within the scope of MDS, are sufficient to measure information about species present in a population.

The detection of de novo mutations in a culture of *E. coli* grown in the lab is a particularly difficult challenge for metagenomic sequencing. MDS was tested on in vitro synthesized DNA to test its accuracy. The results of this test are reproduced in FIGS. 1B and C. The protocol herein enables detection of variants in rpoB, in particular the region most commonly associated with rifampicin resistance. This method works on samples with a high level of homogeneity and a small amount of "interesting" variation. As a result, one of ordinary skill could substitute *Mycobacterium tuberculosis* (MTB) isolated from a patient's sputum for the *E. coli* cultures here. In this situation, MDS could be used to detect rifampicin-resistant bacteria on a timescale several days faster than the best existing methods, which rely on culturing slow-growing MTB in rifampicin-containing media.

If rifampicin-resistant clones were detected using MDS, a clinician would know to prescribe a cocktail of drugs without rifampicin, possibly preventing a drug-resistant strain from taking over. MDS is also useful for comprehensive detection of bacterial populations outside of a human body, such as in a hospital, home, or in the wild. Such and other similar modifications to the preferred embodiment of Maximum Depth Sequencing for this application to customization of patient metagenomics should be apparent to a person having ordinary skill in the art, and hence the details are not repeated here.

Cancer Prognosis and Treatment

Cancer is a highly heterogeneous disease. When MDS is applied to DNA from cells harvested from a tumor biopsy, circulating tumor cells (CTCs), or circulating tumor DNA (ctDNA), it can assess the heterogeneity of the tumor, giving information about both its drug-resistance properties as well as its general progression. In particular, the "liquid biopsy" provided by circulating tumor cells has shown promise as a means of analyzing the properties of the tumor post-treatment in fast-recurring cancers, such as colorectal cancer, minimal residual disease in leukemia, and small-cell lung cancer. It has also been recently shown that chemotherapy-resistant subpopulations of cancer often exist in the primary tumor and prior to treatment, indicating that a deep-sequencing method such as MDS could predict cancer treatment outcomes before chemotherapy is applied.

Numerous chemical biomarkers and detection methods based on cell-surface proteins of circulating tumor cells exist. However, these markers provide only rough information about the existence and state of the cancer. DNA-based methods, such as qPCR and more recently, digital droplet PCR, have been shown to be sensitive methods for detecting a single type of mutation present in a sample. However, they can only be used to detect mutations that are well characterized and for which selective primers have been synthesized. Because genomic diversity itself can be a better predictor of tumor progression than the presence of specific mutations, a mutation-agnostic method such as MDS may provide more accurate information about the state of cancer progression than the aforementioned methods. Recently, standard barcode-based deep sequencing of immune cells revealed pre-leukemic cells. As MDS affords an accuracy and yield that are higher than standard barcoding, it is clear that MDS would be a useful method for this exact application.

Classical cancer genes such as TP53, KRAS, and EGFR are obvious targets for MDS. One of ordinary skill will understand that other targets may be identified by study of tumor genetics and chemotherapy resistance. MDS will be a suitable screening tool for any such targets. Cancers that may be screened for by MDS include carcinoma, melanoma, lymphoma, blastoma, leukemia, myeloma, sarcoma or germ cell tumors.

When MDS detects a high level of mutational heterogeneity in any of the cancer genes it is applied to, it can inform physicians as to the stage of the tumor. This enables the physician to check for malignancies or prescribe more aggressive forms of treatment if the disease has progressed.

Kits

Another aspect of the present disclosure relates to a kit for performing the MDS. In some embodiments, the kit comprises an adapter barcode primer, an adapter reverse primer, a forward adapter amplifier primer, and a reverse adapter amplifier primer for a region of interest in the genome of an organism. In some aspects, the kit further comprises an endonuclease. In some aspects, the kit further comprises a PCR mix and a DNA polymerase.

Below are disclosed methods, materials and procedures for the practice of an embodiment of the invention. One of ordinary skill will understand that the invention is not limited to the below disclosed methods, materials and procedures. One of ordinary skill will understand that the invention may be performed with the many variations and adaptations of PCR DNA amplification known in the art. One of ordinary skill will understand that the embodiments of the present application are not limited to methods using only a single bar code primer, but rather specifically envisions alternate approaches such as using more than one barcoded primer. One of ordinary skill will understand that the invention may also be performed using alternative modes of DNA amplification, including ligase chain reaction (LCR), transcription-mediated amplification (TMA), nucleic acid sequence-based amplification (NASBA), strand displacement amplification (SDA), self-sustained sequence replication (3SR), rolling circle amplification (RCA), loop-mediated isothermal amplification (LAMP), recombinase polymerase amplification (RPA), and Q-beta replicase amplification. One of ordinary skill will understand that the invention may be used in conjunction with therapeutic and diagnostic approaches relevant to specific cell types in both plants and mammals. Further aspects and advantages of the application will appear from the following description taken together with the accompanying drawings.

EXAMPLES

Example 1

Methods and Materials

Preparation of DNA Samples

Genomic DNA Preparation: Spin down up to 5 mL of bacterial liquid culture (see later section for specific growth conditions). Resuspend cells in 500 µL Tris-EDTA buffer (pH 7.5). Add 1000 units of Ready-Lyse (Epicentre). Incubate at room temperature for 1 hour. Freeze in −80° C. overnight. Perform genomic DNA extraction using Qiagen genomic tip (100G), but without lysozyme. Quantify using Nanodrop.

In vitro DNA Preparation: Single-stranded oligos with sequences corresponding to MG1655 rpoB at position 1511-1632 and mrcA at 1258-1379 were ordered from IDT and resuspended in deionized water. These oligos were used directly as input to the Extreme-depth sequencing protocol above for calculation of error rate in FIG. 1, panel C and the "Negative Control" rows in Table 1.

Separately, 10 ng of the same DNA oligos were used as templates for a standard 20-cycle exponential PCR reaction with only the [primer] component of the forward and reverse primers above using either Q5 or Phusion polymerase.

The amplified DNA was used as input into the Extreme-depth sequencing protocol and used to calculate the intrinsic substitution error rate of those two polymerases as reported in Table 1.

*E. coli* Growth Protocol for Extreme-depth Sequencing Experiments

*E. coli* were streaked onto Luria-Bertani (LB) Agar from freezer stocks and grown at 30° C. for 24 hours. According to plating and colony-forming unit (CFU) counting, the average number of cells in such colonies is $3 \times 10^8$ (thus the number of generations is $\ln(3 \times 10^8) = 19.5$. Bacteria from a single colony were used to inoculate a small liquid culture (1 ml LB broth in a round-bottom tube). For the purposes of generation counting, it is assumed that after the transition to growing in liquid, growth occurs for only ~3 generations, since the number of bacteria in the colony is roughly equal to the carrying capacity of the broth. The culture was grown for 12 hours on a 37° C. shaker.

4 μL (~$10^7$ bacteria) were transferred to a fresh 100 mL LB liquid culture (in a 250 mL Erlenmeyer flask). Liquid cultures were grown for 24 hours on a 37° C. shaker, to a density of $2.5 \times 10^9$ bacteria according to cell counts (for a total of $2.5 \times 10^{11}$ bacteria). This process was performed 9 times. The average number of generations a bacterium would have grown in each liquid culture is $$\ln\left(\frac{2.5 \times 10^9}{10^7}\right) = 10.1 \text{ generations}$$

Thus the average total number of generations is $19.5 + 3 + 9 \times 10.1 = 113$.

Four biological replicates of each condition were grown. All liquid cultures, including the small founding culture, had the possible addition of 1 μL/mL ampicillin or 15 ng/mL norfloxacin. It is worth noting that by using a large population to inoculate each new liquid culture, the probability that any two bacteria have the same founder in the inoculant is greatly reduced. The fact that most of the "interrelatedness" between bacteria sampled at the end of the culture is important for the way mutation rate is calculated. Significantly, the fact that certain regions of the genome may replicate earlier (and thus have more copies than others) has a negligible impact on the calculation of mutation rate because the number of extra divisions provided by such an event is small when compared to the total number of generations the bacteria have been grown in broth.

Mock Culture and ≤20 Generation Growth Assay

Wild type *E. coli* and those with point mutations in the rpoB ROI isolated from Rif-resistance fluctuation assays (see below) were streaked, incubated, and inoculated into 1 mL liquid cultures as above. After growth for 12 hours, genomic DNA was immediately extracted. Mutant DNA was added to a background of WT DNA according to the concentrations in Table 2. For analysis of substitution frequencies at ≤20 generations nucleotide positions corresponding to the spiked-in mutants were excluded from analysis.

TABLE 2

| rpoB position | WT | mutant | input concentration | recovered concentration |
|---|---|---|---|---|
| 1598 | T | C | 1.00E−02 | 1.69E−02 |
| 1592 | C | T | 1.00E−02 | 2.22E−02 |
| 1586 | G | A | 1.00E−02 | 7.79E−03 |
| 1538 | A | T | 1.00E−03 | 1.79E−04 |
| 1576 | C | T | 1.00E−03 | 8.84E−04 |
| 1577 | A | T | 1.00E−04 | 7.01E−05 |
| 1547 | A | G | 1.00E−04 | 1.07E−04 |

TABLE 2-continued

| rpoB position | WT | mutant | input concentration | recovered concentration |
|---|---|---|---|---|
| 1535 | C | T | 1.00E−04 | 5.11E−05 |
| 1576 | C | G | 1.00E−05 | 4.71E−06 |
| 1547 | A | T | 1.00E−05 | 4.57E−06 |
| 1565 | C | T | 1.00E−05 | 5.71E−06 |
| 1576 | C | A | 1.00E−06 | 8.65E−07 |
| 1534 | T | C | 1.00E−06 | 1.76E−06 |
| 1546 | G | A | 1.00E−06 | 6.92E−08 |

Strains

MG1655 *E. coli* were used as wild-type cells for all experiments. The tet-regulated mrcA strain MG1655(CmR:: Ptet-mrcA SpR::tetR) was prepared according to Lutz, R.; Bujard, H. (1997) Independent and tight regulation of transcriptional units in *Escherichia coli* via the LacR/O and the TetR/O and AraC/$I_1$-$I_2$ regulatory elements. Nucleic Acids Research. 25(6):1203-10. For details on the catalase overexpression mutant and inactive H106Y catalase overexpression mutant see Dwyer, D. J. et al. (2014) Antibiotics induce redox-related physiological alterations as part of their lethality. PNAS 111(20):E2100-E2109, doi: 10.1073/pnas.1201876111. Mutant strains were induced with anhydrous tetracycline at 50 ng/ml. In the mutS knockout strain, MG1655 mutS was replaced with a kanamycin resistance cassette.

Reagents are as follows:
1) DNA of interest
2) Restriction Enzyme with appropriate buffer (see below for specifics)
3) High-fidelity Polymerase with appropriate reaction mix (Q5 or Phusion from New England Biolabs)
4) Adapter-barcode-primer (see below for specific primer schema)
5) Exonuclease I (NEB)
6) PCR Purification Kit (Thermo)
7) Additional primers for amplification (forward adapter amplifier, adapter-reverse-primer, and reverse adapter amplifier)
8) Ampure XP beads (Agencourt)

Although 14-mer random barcodes (with either A, C, T, or G at each location in equal probability) are used, barcodes with balanced AT/CG content would slightly increase yield.

Bead/droplet technology can be used for tiling over a longer region. MDS is highly compatible with methods for tagging longer fragments of DNA with the same molecular barcode using beads and droplets. In this situation, genomic DNA is first isolated into individual droplets with beads, each containing a unique set of primers with the same barcode. Digestion with restriction enzyme or cas9 occurs inside the droplets to maintain colocalization of genomic DNA from the same original fragment to the same bead. The primers on the bead are protected from restriction digestion because they are single stranded. The restriction enzymes are heat-deactivated. Finally, a single PCR step, without the need for a reverse primer, is performed to "attach" the original genomic DNA molecule to the beaded primers. At this point all DNA can be dissociated from the beads, mixed, and MDS proceeds with linear amplification as normal.

Equipment is as follows:
1) Nanodrop (Thermo Scientific)
2) Thermocycler
3) Heat block
4) HiSeq (Illumina)
5) Optional: TapeStation (Agilent Technologies, Inc)

The steps of the procedure may be as follows:
0. Restriction digest.
a. Incubate 1 µg DNA in 50 µL 1× restriction enzyme buffer with the appropriate amount of restriction enzyme. For this study, 1 unit XmnI was used. Samples were incubated at 37° C. overnight.
b. Deactivate restriction enzyme. For XmnI, samples were heated at 65° C. for 20 minutes.
1. 1 cycle PCR with adapter-barcode-primer
a. Prepare 50 µL PCR reaction mix using adapter-barcode-primer and 12.5 µL of the sample above (250 ng DNA)
b. PCR, 1 cycle: 98° C. 1 min, 60° C. 15 sec, 72° C. 1 min
2. Remove unused barcodes
a. Immediately add 1 µL exonuclease I+5 µL buffer.
b. Incubate at 37° C. for 1 hr, then 80° C. for 20 min
c. Clean sample using PCR purification kit
3. Linear amplification using forward adapter amplifier primers
a. Add cleaned DNA to fresh 50 µL reaction mix with forward adapter amplifier primer.
b. PCR, 12 cycles: 98° C. 15 sec, 61° C. 15 sec, 72° C. 5 sec
Note: The number of linear amplification cycles is limited by off-target amplification.
4. Exponential PCR
a. Add adapter-reverse-primer and reverse adapter amplifier primers.
b. PCR, 15 cycles: 98° C. 15 sec, 61° C. 15 sec, 72° C. 5 sec
5. Purify with Ampure XP beads
Optional: If using multiple samples with phased barcodes, combine DNA first in equimolar concentrations. For this study, quantification at this step was done using TapeStation.
6. Sequence. HiSeq Rapid Run, 150 bp, Paired-End.

In vitro cas9 targeting allows guide RNA to target any conceivable location in the cell. This overcomes the need for a restriction enzyme to target a particular region of interest (ROI). For example, the protocol is modified to shift the ROI one base pair downstream (to the 1512 position of rpoB), by modifying step 0 of the procedure as follows. Instead of digesting with XmnI, digestion occurs with CRISPR/cas9, using a guide RNA to be complementary to the sequence 3 bp upstream of the 1512 position (CCGATTTCCGCAGCAGTGAA (SEQ ID NO: 1)) followed by the protospacer adjacent motif. In vitro cas9 digestion kits can be purchased from New England Biolabs.

Example 2

Primer and Restriction Schema for rpoB Analysis

Mutation rates were investigated in MG1655 E. coli grown for ≤120 generations, before selective sweeps are expected to occur and, importantly, long before selection for a hyper-mutating strain might be expected. Two ~100 nucleotide ROIs were investigated: one in a region of rpoB conferring rifampicin resistance so that our results can be directly compared to those from fluctuation assays, and one in mrcA, a nonessential gene with mRNA expression estimated at 0.02 molecules/cell.

The region of rpoB at position 1511-1632 was analyzed. XmnI cuts before the 1511 position of rpoB. The following primers were used for the procedure (Note: Nx14 refers to the 14mer random sequence, which varies within a sample, for a total of 4^14=268,435,456 possible barcodes. All primers were from IDT. Restriction enzymes were from NEB):

Adapter-barcode-primer: [P5][Rd1Seq primer segment][barcode][primer]
(SEQ ID NO: 2)
[AATGATACGGCGACCACCGA][GATCTACACTCTTTCCCTACACGACGCTCTTCCGATCT][Pad][Nx14][AGTTCTTCGGTTCCAGCCAGC]

Forward adapter amplifier:
(SEQ ID NO: 3)
AATGATACGGCGACCACC

Adapter-reverse-primer: [P7][Rd2Seq primer segment][primer]
(SEQ ID NO: 4)
[CAAGCAGAAGACGGCATACGA][GATCGGTCTCGGCATTCCTGCTGAACCGCTCTTCCGATCT][Pad][CCTGCACGTTCACGGGTC]

Reverse adapter amplifier:
(SEQ ID NO: 5)
CAAGCAGAAGACGGCATAC

In the above primer sequences, Pad refers to 0-7 nucleotides of sequence ACGTACG (SEQ ID NO: 6). Because Illumina sequencing machines typically perform better when a given sequencing cycle is less homogenous, 8 rpoB samples were prepared. Analysis used the pads to index sequence reads from different trials and experiments. Typically for robustness when the forward pad is M nt long, the reverse pad is 7−M nt long.

Example 3

Analytical Methodology

After grouping by barcode, sequences were aligned using the forward and reverse [primer] sequences for mrcA and rpoB above. Samples were indexed according to phase. Consensus bases, including indels, are called only when all bases at a given position and barcode have 100% agreement.

For analysis of the polymerase error rate only, because of the high rate of indels in chemically synthesized DNA, all indels and reads with more than one deviation from the wild type sequence were excluded. The low rate of Phusion indels has been confirmed in previous studies.

Sources of error include damaged DNA during extraction, polymerase errors during PCR, and sequencing errors. Since the goal is to identify rare mutants, the error rate is considered the rate of false positives, which affect mutant frequency to a larger extent than false negatives. One of ordinary skill will understand that a variety of computational techniques can be used to enhance the detection of rare variants, see, e.g., Newman et al., Nature Biotech., 34, 547-555 (2016); Gerstrung et al., Nature Comms., 3, Article No. 811, doi:10.1038/ncomms1814, (2012).

If the probability of a single nucleotide X being misread as Y due to polymerase error is $P_{pol,x \to y}$ and the rate of the corresponding sequencing error is $P_{seq,x \to y}$, then the probability that X will be read as Y due to either source of error in a standard sequencing protocol is: $P_{x \to y} = P_{pol,x \to y} + P_{seq,x \to y}$.

The total polymerase error rate $E_{pol,x \to y}$ can be derived as follows. After exponential PCR, there are N pools of reads, each derived from one of the original linear amplification steps. Assuming $p = P_{pol,x \to y} \ll 1$ the probability of having k pools derive from an original polymerase error can be approximated by a Poisson distribution.

$$\binom{N}{k} p^k (1-p)^{N-k} \approx \frac{(Np)^k}{k!} e^{-Np}$$

The probability of a false positive is the probability that all R reads used to form a consensus came from one of the k "error" pools $$\sum_{k=1}^{\infty} \frac{1}{N^R} k \frac{(Np)^k}{k!} e^{-Np} = \frac{1}{N^R} Np \sum_{k=1}^{\infty} \frac{(Np)^{k-1}}{(k-1)!} e^{-Np} = \frac{p}{N^{R-1}} \sum_{k=1}^{\infty} \frac{(Np)^k}{k!} e^{-Np}$$

Thus, the probability of false positive is $$E_{pol,X \to Y} = \frac{P_{pol,X \to Y}}{N^{R-1}}$$

The error rate of sequencing after forming a barcode, as discussed in Kinde, I.; Wu, J.; Papadopoulos, N.; Kinzler, K. W.; Vogelstein, B. (2011) Detection and quantification of rare mutations with parallel sequencing. PNAS. 108(23) 9530-9535. doi: 10.1073/pnas.1105422108; and in Lou, D. I. et al. High-throughput DNA sequencing errors are reduced by orders of magnitude using circle sequencing. PNAS 110(49):19872-7; is the probability that the same error happens Ř times $$E_{seq,X \to Y} = (P_{seq,X \to Y})^{\check{R}}$$

Where Ř is the number of "not necessarily independent" reads used to form a consensus (i.e. overlapping paired-end sequences of the same read are included). More precisely, analysis of R independent reads means a maximum of Ř=2R not necessarily independent reads are used. Alternatively, one could estimate $E_{seq,x \to y}$ based on the sum of quality scores of the Ř reads contributing to the consensus, but in practice this is unnecessary because sequencing errors are not the major contributor to overall error when R>2.

The total error rate in the protocol can be approximated as $$E_{X \to Y} = \frac{P_{pol,X \to Y}}{N^{R-1}} + (P_{seq,X \to Y})^{\check{R}}$$

The total error rate for any given nucleotide position is the sum of all the error rates (Ex->y), where the nucleotide at that position is a false positive (X≠Y), for that given nucleotide position (X). The values reported herein and FIG. 1C are total error. Extrapolation of error rate for each substitution X->Y given sequencing error rates is shown in Minoche, A. E.; Dohm, J. C.; Himmelbauer, H. (2011) Evaluation of genomic high-throughput sequencing data generated on Illumina HiSeq and Genome Analyzer systems. Genome Biology. 12:R112. doi: 10.1186/gb-2011-12-11-r112. Raw polymerase and sequencing error rates are shown in Table 1.

Mutation rates in the assay are chosen to maximize the likelihood of recovering the mean mutant frequency for substitutions of a given type X->Y, which occur a Poisson process over a certain number of generations (in this case 113).

$$\mu_{X \to Y} = \frac{freq(Y) - E_{X \to Y}}{\# \text{ generations}}$$

Figure 3:
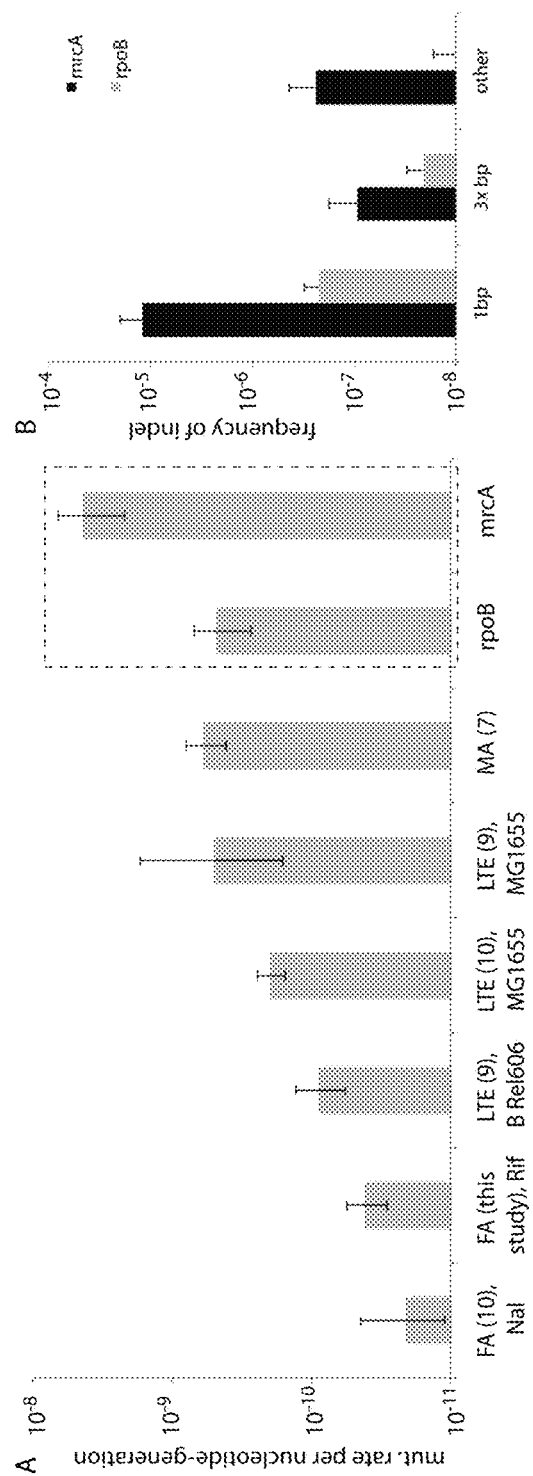
FIG. 3 is a set of exemplary illustrations of substitution rates and indel frequencies. (Panel A) Comparison of mutation rates calculated from fluctuation assays (FA) using either rifampicin (Rif) or nalidixic acid (Nal), long-term evolution (LTE), and mutation accumulation (MA). Rates calculated using MDS are boxed. (Panel B) Frequency of indel mutations recovered at t=120 generations. Values are normalized for possible indel lengths considered in each category.

Mutation rates given in FIG. 3 are computed from the average across all x of $$\Sigma_{Y \forall Y \neq X} \mu_{X \to Y}$$

with C->A, G->T, C->T, and G->A substitutions excluded for aforementioned reasons.

Example 4

Analysis of rpoB Mutation

Figure 6:
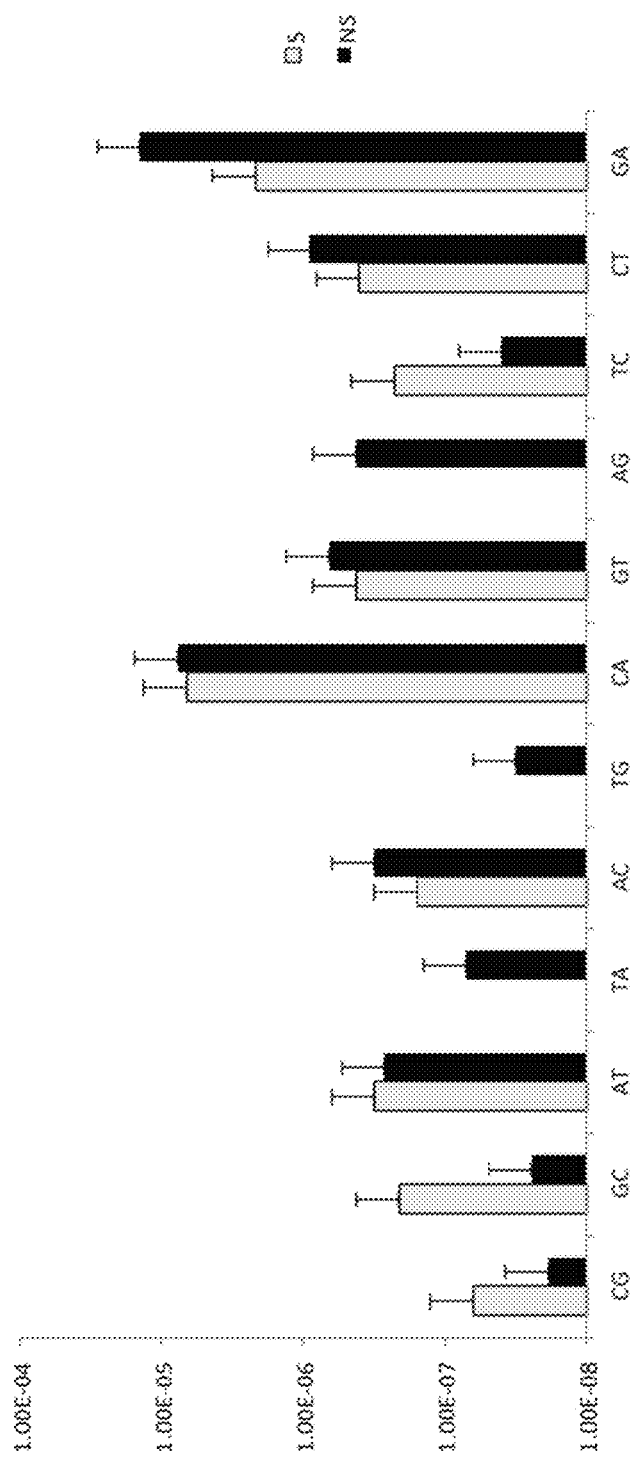
FIG. 6 is an illustration of substitution frequencies separated by synonymous (S) and nonsynonymous (NS) substitutions in rpoB. Note that because the number of possible synonymous substitutions is less than the number of possible nonsynonymous substitutions, the detection limit for nonsynonymous substitutions is lower. Error bars are upper bound 95% CI.

The calculated rate of mutation in rpoB is $4.8 \times 10^{-10}$ nucleotides/generation, comparable to the rate obtained in mutation accumulation experiments and at least one long-term evolution experiment using MG1655. Yet it is also higher than other rates calculated by fluctuation assay and long-term evolution on other strains (FIG. 3, panel A). Traditional rifampicin-based fluctuation assays were performed and a similar spectrum and low rate of mutation to others was recovered using such approaches (FIG. 3, panel A). It is likely that the higher rate of mutation in rpoB obtained with MDS indicates a rate uninfluenced by negative selection, phenotypic lag, or imperfect plating efficiency. Note that although the mutation rate is calculated using only synonymous substitutions, addition of nonsynonymous substitutions does not change the rate significantly (FIG. 6). Remarkably, the calculated rate of mutation in mrcA is $4.4 \times 10^{-9}$ nucleotides/generation, is an order of magnitude higher than the observed rate in rpoB (p<0.001 by T-test). Comparison of genomes from several *E. coli* strains has suggested that the rate of substitution varies across the genome and that highly transcribed genes appear to be protected by an unknown mechanism. These results demonstrate that at least one gene with low transcription rate has significantly higher mutation rate than another with high transcription rate under normal growth conditions.

Figure 4:
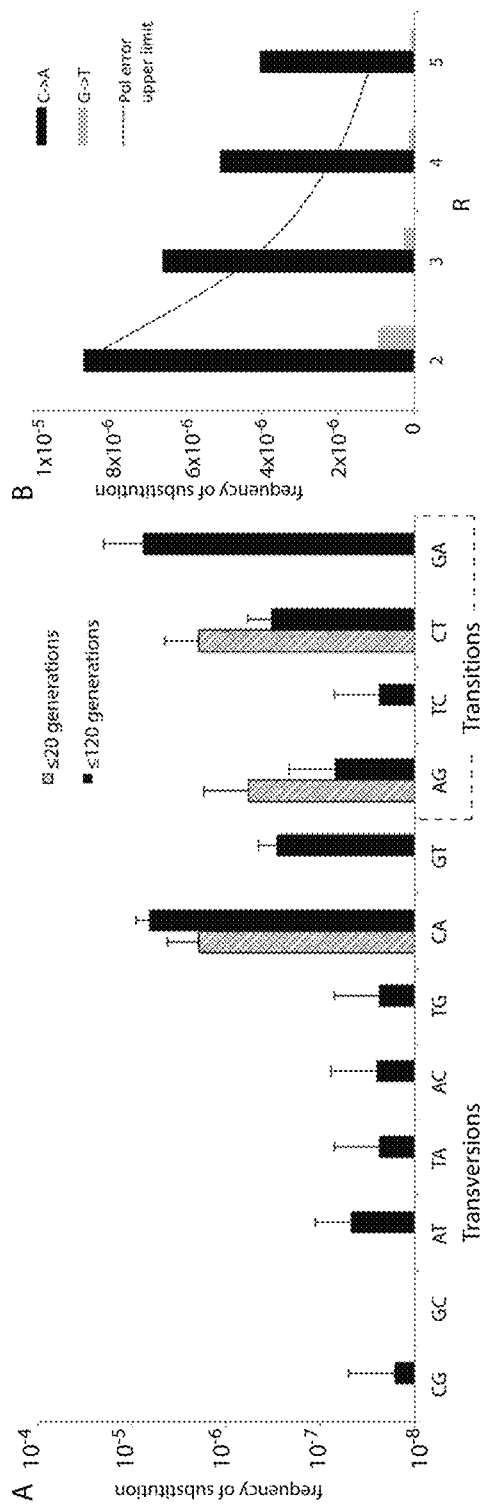
FIG. 4 is a set of exemplary illustrations of substitution spectra. (Panel A) Frequency of base substitutions recovered in the sequencing protocol at t=20 generations and t=120 generations in rpoB. Error bars are 95% CI upper bound. (Panel B) The high frequency of C->A substitutions is consistent even as R increases. If these substitutions were polymerase errors due to damaged nucleotides, they should decline with increasing R faster than the line shown.

The mutational spectrum from MDS matches that found in long-term sequencing experiments, with transition mutations favored over transversions (FIG. 4, panel A). There is an unexpected high frequency of C->A substitutions. These appear not to be lasting mutations, as complementary G->T substitutions emerged with less than 0.1-fold frequency. A similar effect was found to a lesser extent for G->A/C->T substitutions. Increasing R did not significantly reduce these high substitution frequencies (FIG. 4, panel B), suggesting that the majority of C->A substitutions are not due to damaged nucleotides, such as 8-oxo-Gs. Instead, it appears that As, or rAs, are misincorporated into the genome at C sites. In vivo these misincorporations must be reversed before genome replication. These observations represent a snapshot of this dynamic process before repair can occur. Although these events would be invisible to conventional methods, the frequency of these substitutions, at ~$10^{-5}$ per nucleotide, is over $10^4$ times more frequent than the true rate of mutation.

To clarify which substitutions are transient vs. involved in "true" mutation, DNA was analyzed from bacteria harvested after ≤20 generations, a short enough time period to where few true mutations are expected given the sample size (FIG. 4, panel A). Enrichment was observed for most types of substitutions in the ≤120 generation trial over the ≤20 generation control, as would be expected from true mutations. However, C->A, A->G, and C->T substitutions occur in comparable frequency in the 20 and 120 generation trials, suggesting these substitutions reflect a continual process of base misincorporation and repair. These abundant A and T substitutions were not included in the calculation of mutation rates. However, these findings suggest a mechanism for how E. coli grown in lab for a long period of time can experience an increase in AT content at neutral sites.

A short (≤12 bp) indel rate in mrcA of $1.2 \times 10^{-9}$/nucleotide-generation was calculated. However, even within mrcA, an indel rate varies by position and length. As might be expected, 100% of the observed 1 bp indels occurred at a site adjacent to a homopolymer. Longer indels followed no such pattern.

Single nucleotide indels and longer frame-shifting mutations were also observed in rpoB, albeit at less than 0.1-fold frequency, even though such mutations should be deleterious. As expected, in rpoB, the rate of in-frame indels was higher than the rate of frameshift indels (FIG. 3, panel B). Because of the low rate of indel errors from in vitro polymerases such as Phusion, it is plausible that the observed frameshift mutations are from inviable bacteria. Such cells are not prevented from entering the procedure. Both the recovery of single nucleotide indels and the insignificant difference between rates of synonymous and non-synonymous substitutions in rpoB demonstrate that selection during the procedure is minimal. In both mrcA and rpoB deletions of all lengths were detected at >10-fold frequency of insertions.

Example 5

Effect of Antibiotics on Mutation Rate

The effect of sub-inhibitory doses of antibiotics of different classes on mutation rate was investigated using both MDS and detailed fluctuation assays as performed in Garibyan, L. et al. (2003). DNA Repair. 2(5):593-608; and Lang, G. I.; et al. (2008). Genetics 178(1):67-82. Addition of ampicillin resulted in an increase in the rate of transition mutations in rpoB, a signature indicative of down-regulated mismatch repair. In cells overexpressing catalase, basal mutation rate decreased by a factor of 8, indicating that background oxidation contributes significantly to the basal mutation rate under non-stressed conditions. Addition of ampicillin did not increase this lower rate in the presence of extra catalase. Overexpression of a catalase with inactivating point mutation H106Y did not confer similar protection against mutagenesis. These results support a model in which ampicillin causes oxidative stress, which in turn leads to down-regulation of mismatch repair, increasing the mutation rate. Consistent with this model, cells grown in anaerobic conditions did not display an increase in transition rate when challenged with ampicillin. The same was true in aerobic conditions if mismatch repair gene mutS was knocked out.

Interestingly, addition of ampicillin increased transversions and indel formation in mrcA, but not in rpoB. It is known that mrcA undergoes mild induction upon addition of ampicillin. The increase in transcription may be responsible for the broad increase in mutagenesis.

Exposure to norfloxacin increased the transition substitution rate in rpoB, although it may be noted that in fluctuation assays, this increase was only seen in cells that were grown to stationary phase. This discrepancy indicates that rpoS is a key mediator between levels of oxidative stress and levels of mutation. Exposure to norfloxacin increased the rate of >1 bp indel formation in both mrcA and rpoB. It is known that norfloxacin inhibits DNA gyrase and can result in double-strand breaks in DNA. These results indicated that such a physical interaction can directly cause antibiotic-induced mutagenesis in norfloxacin-treated cells.

Example 6

Impact of Transcription on Mutagenesis

There is debate as to whether highly transcribed genes in bacteria have a rate of mutagenesis that is higher, or lower than that of other genes. Analysis of MG1655 E. coli shows that mrcA has a higher rate of mutation than rpoB, a more highly transcribed gene under non-stressed conditions, yet induction of mrcA by ampicillin increases the rates of substitution and indel formation. The impact of transcription on mutagenesis in a more controlled manner was analyzed using MDS. An E. coli strain was created in which a chromosomal copy of mrcA is regulated by a tetracycline promoter. When mrcA transcription was induced in this strain, all classes of mrcA substitution and indel increased in frequency. This increase was ~3-fold greater than when wild-type cells were exposed to ampicillin, consistent across all categories of mutation. These results suggest that co-directional collisions between transcription and replication machinery are themselves a source of mutagenesis. Indeed, co-directional collisions between backtracked RNA polymerase and replisome often result in double strand breaks, a source of mutations due to the error-prone repair process. mrcA, which lacks a canonical Shine-Dalgarno sequence and uses GTG rather than ATG as a start codon, is translated at a much lower rate than rpoB. Because active ribosomes normally prevent RNA polymerase backtracking, poor translation of mrcA could explain both its sensitivity to transcription-induced mutagenesis as well as highly transcribed and translated rpoB's low basal mutation rate.

The increase in indel rate in mrcA upon addition of ampicillin may thus be due to increased transcription, but many genes are induced in response to stress. Induction itself may thus be an important mechanism of stress-induced mutagenesis. Although such changes would be impossible to detect using fluctuation assays, they would have important implications for bacterial diversity in response to stress such as antibiotics.

The foregoing descriptions of specific embodiments of the present application have been presented for purposes of illustration and description. They are not intended to be exhaustive or to limit the application and method of use to the precise forms disclosed. Obviously many modifications and variations are possible in light of the above teaching. It is understood that various omissions or substitutions of equivalents are contemplated as circumstance may suggest or render expedient, but is intended to cover the application or implementation without departing from the spirit or scope of the present application.

What is claimed is:

1. A method for sequencing DNA in the genome of an organism, comprising:
   (a) digesting genomic DNA of the organism with an enzyme that cleaves at the 3' end of a region of interest (ROI) to produce digested genomic DNA;
   (b) forming a mixture comprising the digested genomic DNA and an adapter barcoded primer, wherein the adapter barcoded primer comprises, from 5' to 3', an adapter region, a barcode region and an annealing region that anneals at the 3' end of the ROI and performing a single round of extension using the mixture to produce a single round extension product containing a strand comprising, from 5' to 3', the ROI, a first sequence that is complementary to the barcode region and is attached to the 3' end of the ROI, and a second sequence complementary to the adapter region;
   (c) performing N cycles of linear amplification using the strand obtained in (b) as a template and a forward adapter amplifier primer to produce a linear amplification product;
   (d) performing exponential polymerase chain reaction (PCR) with the linear amplification product to produce an amplified product using at least two primers; and
   (e) sequencing the amplified product.

2. The method of claim 1, further comprising the step of aligning the sequences obtained in step (e) to quantify mutations in the ROI.

3. The method of claim 1, wherein the genomic DNA of the organism is digested with a restriction enzyme.

4. The method of claim 1, further comprising the step of removing unused barcoded primers from the single round extension product.

5. The method of claim 1, wherein the forward adapter amplifier primer shares a region of homology with the adapter region of the adapter barcoded primer.

6. The method of claim 1, wherein N is an integer equal to or greater than 8.

7. The method of claim 1, wherein N is an integer equal to or greater than 16.

8. The method of claim 1, wherein the pair of primers used in (d) include a first primer that hybridizes at the adapter region and a second primer that hybridizes at the 5' end of the ROI.

9. The method of claim 1, wherein the forward adapter amplifier primer is the only primer used in step (c).

* * * * *

UNITED STATES PATENT AND TRADEMARK OFFICE
CERTIFICATE OF CORRECTION

PATENT NO. : 10,513,732 B2
APPLICATION NO. : 15/207051
DATED : December 24, 2019
INVENTOR(S) : Justin Jee, Bhubaneswar Mishra and Evgeny Nudler Page 1 of 1

It is certified that error appears in the above-identified patent and that said Letters Patent is hereby corrected as shown below:

On the Title Page

Item (12) "Lee et al." should read -- Jee et al. --.

Item (72) correct the spelling of the first inventor's name, under Column 1, Line 4 as follows:
Inventors: Justin Jee, New York City, NY (US);

Signed and Sealed this
Second Day of June, 2020

Andrei Iancu
*Director of the United States Patent and Trademark Office*

SEQUENCE LISTING

<160> NUMBER OF SEQ ID NOS: 6

<210> SEQ ID NO 1
<211> LENGTH: 20
<212> TYPE: DNA

```
<213> ORGANISM: Artificial Sequence
<220> FEATURE:
<223> OTHER INFORMATION: Synthetic: Guide RNA

<400> SEQUENCE: 1
ccgatttccg cagcagtgaa                                              20

<210> SEQ ID NO 2
<211> LENGTH: 100
<212> TYPE: DNA
<213> ORGANISM: Artificial Sequence
<220> FEATURE:
<223> OTHER INFORMATION: Synthetic: Adapter-barcode-primer
<220> FEATURE:
<221> NAME/KEY: misc_feature
<222> LOCATION: (66)..(79)
<223> OTHER INFORMATION: n is a, c, g, or t

<400> SEQUENCE: 2
aatgatacgg cgaccaccga gatctacact ctttccctac acgacgctct tccgatctac   60
gtacgnnnnn nnnnnnnnna gttcttcggt tccagccagc                        100

<210> SEQ ID NO 3
<211> LENGTH: 18
<212> TYPE: DNA
<213> ORGANISM: Artificial Sequence
<220> FEATURE:
<223> OTHER INFORMATION: Synthetic: Forward adapter amplifier

<400> SEQUENCE: 3
aatgatacgg cgaccacc                                                18

<210> SEQ ID NO 4
<211> LENGTH: 86
<212> TYPE: DNA
<213> ORGANISM: Artificial Sequence
<220> FEATURE:
<223> OTHER INFORMATION: Synthetic: Adapter-reverse-primer

<400> SEQUENCE: 4
caagcagaag acggcatacg agatcggtct cggcattcct gctgaaccgc tcttccgatc   60
tacgtacgcc tgcacgttca cgggtc                                       86

<210> SEQ ID NO 5
<211> LENGTH: 19
<212> TYPE: DNA
<213> ORGANISM: Artificial Sequence
<220> FEATURE:
<223> OTHER INFORMATION: Synthetic: Reverse adapter amplifier

<400> SEQUENCE: 5
caagcagaag acggcatac                                               19

<210> SEQ ID NO 6
<211> LENGTH: 7
<212> TYPE: DNA
<213> ORGANISM: Artificial Sequence
<220> FEATURE:
<223> OTHER INFORMATION: Synthetic: Pad oligonucleotide

<400> SEQUENCE: 6 acgtacg                                                             7
```